United States Patent [19]

Shoor et al.

[11] Patent Number: 4,526,276
[45] Date of Patent: Jul. 2, 1985

[54] APPARATUS AND METHOD FOR SORTING PARTICLES BY GAS ACTUATION

[75] Inventors: Bernard A. Shoor, Atherton; Mack J. Fulwyler, Sunnyvale, both of Calif.

[73] Assignee: Becton, Dickinson and Company, Paramus, N.J.

[21] Appl. No.: 489,667

[22] Filed: Apr. 28, 1983

[51] Int. Cl.³ .......................... B07C 5/34; B07C 5/36
[52] U.S. Cl. .................................. 209/552; 209/606; 209/644; 209/906; 209/932
[58] Field of Search .............. 209/552, 579, 606, 638, 209/639, 644, 906, 932, 933; 239/436, 443

[56] References Cited

U.S. PATENT DOCUMENTS

| | | | |
|---|---|---|---|
| 3,482,686 | 12/1969 | Wood | 209/639 X |
| 3,560,754 | 2/1971 | Kamentsky | 209/906 X |
| 3,791,517 | 2/1974 | Friedman | 209/644 X |
| 3,827,555 | 8/1974 | Kamentsky et al. | 209/644 X |
| 4,175,622 | 11/1979 | Zöld | 209/552 |
| 4,252,240 | 2/1981 | Satake | 209/639 X |
| 4,284,496 | 8/1981 | Newton | 209/44.1 X |

Primary Examiner—Robert B. Reeves
Assistant Examiner—Edward M. Wacyra
Attorney, Agent, or Firm—Richard J. Rodrick

[57] ABSTRACT

An apparatus for sorting particles comprises a nozzle or the like for producing a stream of particles, such as cells, in a liquid flow. The particles are analyzed as they are flowing to detect different parameters thereof. A hollow inner tube and a concentrically arranged hollow outer tube are located downstream of the analyzing area. Gas bubbles are generated in the inner tube to prevent particles from flowing therein and to deflect particles into the annular space between the inner and outer tubes. Gas bubble generation is coordinated with the particle analysis to selectively deflect particles having the different parameters into the annular space, whereby the deflected particles are sorted for collection. A method of sorting particles, such as cells, substantially in accordance with the above-described apparatus is another aspect of the present invention.

17 Claims, 4 Drawing Figures

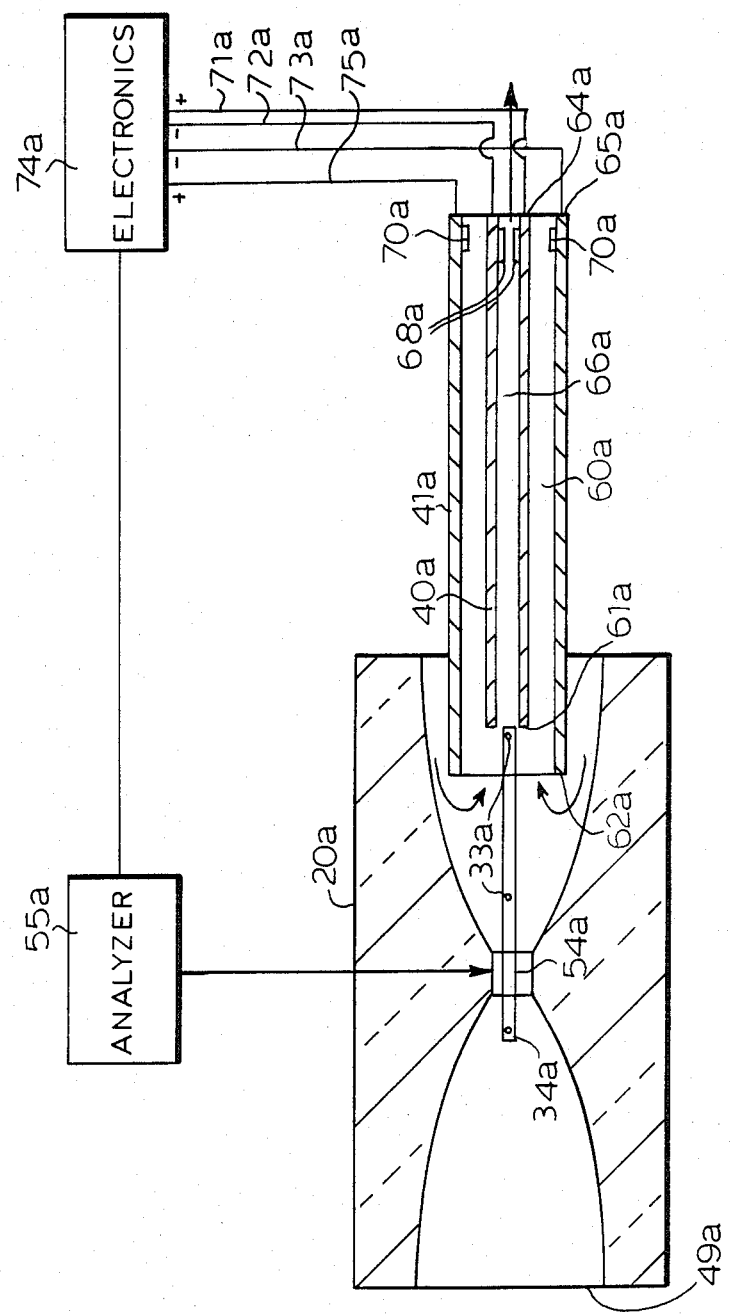

APPARATUS AND METHOD FOR SORTING PARTICLES BY GAS ACTUATION

BACKGROUND OF THE INVENTION

1. Field of the Invention

The present invention relates to an apparatus and method for sorting particles, and more particularly, concerns an apparatus and method for sorting particles moving in a liquid stream, according to differences in particle parameters, by gas actuation.

2. Description of the Prior Art

Flow analysis of particles has been employed in the determination of characteristics of individual particles. Such analysis is most useful in analyzing characteristics of cells for the collection of information which would be useful in areas of research, hematology, immunology and the like. The researcher may be interested, for example, in determining specific characteristics of individual cells so that the cells may be classified, identified, quantified and then sorted for further investigations or analysis. There are a number of well-known cell analysis apparatuses available to the researcher at present utilizing flow cytometry techniques for the measurement of characteristics of individual cells. One such analyzer is known as the FACS ™ Analyzer, sold by Becton Dickinson FACS Systems, Sunnyvale, Calif. Not all available analyzers utilized in flow cytometry, however, analyze the cells and then sort the cells into different categories.

One such sorting apparatus is disclosed by Zold in U.S. Pat. No. 4,175,662. Zold describes a method and apparatus which allows the sorting of particles or cells in accordance with their physical or chemical properties. Sorting is achieved after the particles are analyzed by reliance upon an electrolysis gas impulse which causes a deflection of the particle suspension stream to flow into a different channel. Particles in the different channel, having been sorted, may then be collected separately from particles flowing in the main channel. The method of sorting described by Zold is based on the direct changing of the liquid electrolyte flow path while the suspended particles are deflected only indirectly by the change of the liquid flow.

Application of the particle sorting technique similar to that described by Zold would add a desired improvement to those analyzers which do not have sorting capabilities. However, improvements in the technique as described by Zold would be required in order to assure the compatability of the analyzing features with the sorting features in a flow cytometric apparatus which both analyzes and sorts cells or other particles. It is to such an improvement that the present invention is directed.

SUMMARY OF THE INVENTION

The apparatus for sorting particles of the present invention includes means for transporting particles in a stream. First particle collection means is provided into which the stream is normally directed. Actuatable means prevents particles from passing into the first particle collection means and directs particles into a second collection means surrounding the first particle collection means. This arrangement allows particles to be sorted and, therefore, separately collected.

In a preferred embodiment of this aspect of the present invention, the apparatus sorts particles moving in a liquid stream according to differences in particle parameters. This preferred apparatus includes means for providing a stream of particles in a liquid flow. Means analyze the particles as they are flowing to detect particles having different parameters. A hollow inner tube and a concentrically arranged hollow outer tube are located downstream of the analyzing means. The inner tube has its longitudinal axis aligned substantially with the stream of particles. Means generates gas bubbles in the inner tube to prevent particles from flowing therein and to deflect flowing particles into the annular space between the inner and outer tubes. Further, means coordinates the generation of gas bubbles with the particle analysis to selectively deflect particles having the different parameters into the annular space whereby the deflected particles are sorted for collection.

In another aspect of the present invention, a method of sorting particles includes moving particles in a stream. The stream is normally directed into first particle collection means. Further, the method includes preventing particles from passing into the first particle collection means and directing the prevented particles into second particle collection means surrounding the first particle collection means. In a preferred embodiment of this other aspect of the invention, the method involves sorting particles moving in a liquid stream according to differences in particle parameters. This method preferably analyzes the particles as they are flowing to detect particles having pre-determined parameters. Normally, the particles are directed into the hollow inner tube. Gas bubbles are generated in the inner tube to prevent particles from flowing therein. The method further includes deflecting the flowing particles into an annular space between the inner tube and a concentrically arranged outer tube. Preferably, the present method includes coordinating the generation of gas bubbles with particle analysis to selectively deflect particles having pre-determined parameters into the annular space. Thus, the deflected particles are sorted for collection.

In accordance with the principles of the present invention, a coaxial sorting arrangement is provided which permits ready adaptation of a sorting feature to flow cytometry instruments employed in cell or particle analysis. Accordingly, the present invention provides for the sorting of cells or particles and their ultimate collection into separate containers representing different categories of these cells. Further, the coaxial arrangement of the sorting elements facilitates the deflection of the cells that are moving in the stream. Construction of the coaxial sorting elements, represented by the aforementioned tubes, is simple in technique and straightforward in assembly, and therefore serves to improve the technique described by Zold which relies upon deflection of flowing particles to achieve sorting.

BRIEF DESCRIPTION OF THE DRAWINGS

FIG. 4 is an enlarged sectional view similar to the view of FIG. 2 illustrating an alternative embodiment of the gas actuating elements.

DETAILED DESCRIPTION

Figure 1:
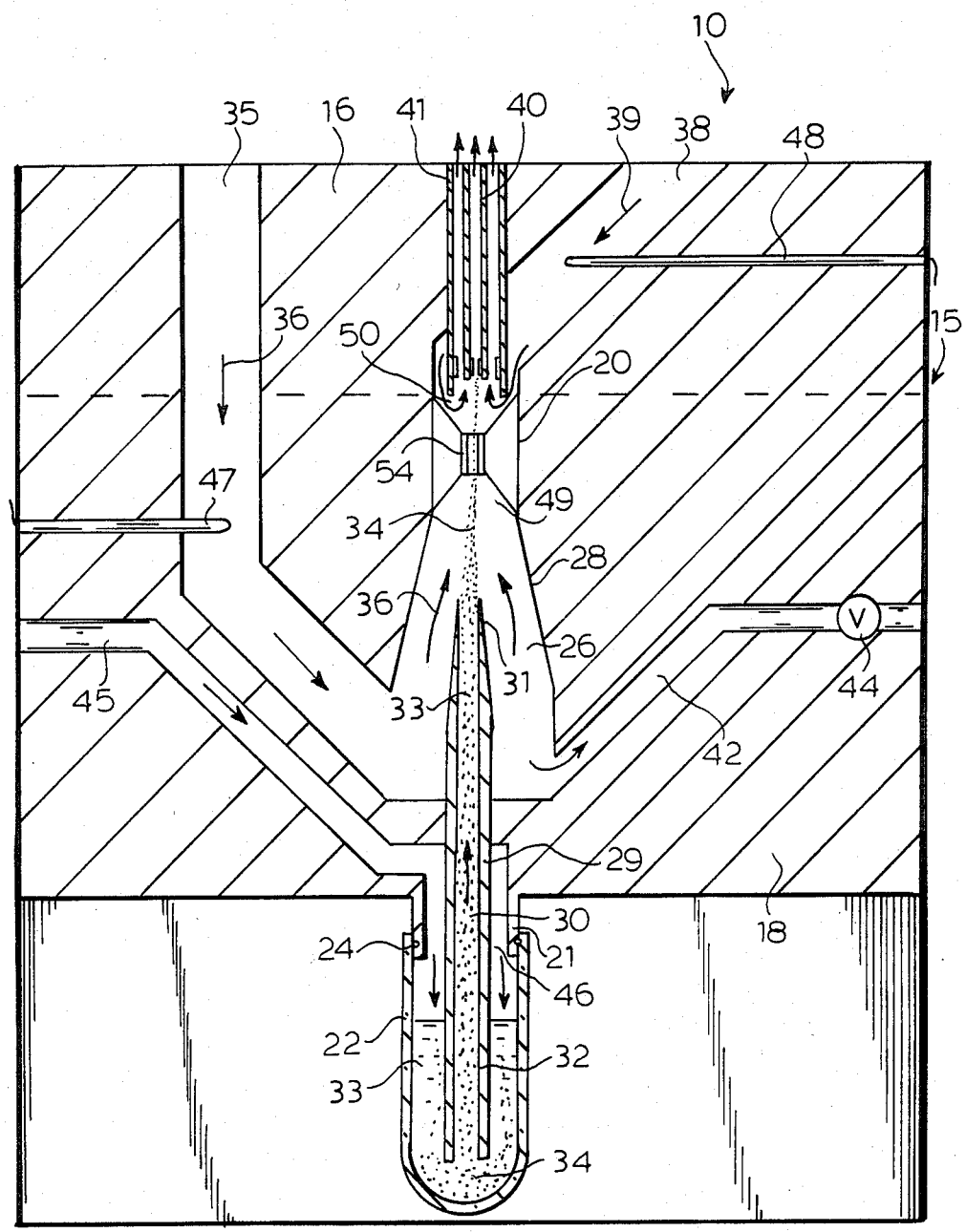
FIG. 1 is a schematic illustration of the liquid flow paths of a particle sorting apparatus of the present invention, this apparatus also adapted to analyze certain parameters of the moving particles.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings, and FIG. 1 in particular, there is illustrated a schematic representation of the liquid flow paths of particles, such as cells in a combined analyzing and sorting apparatus in accordance with the present invention. The improved sorting features of the present invention provide advantageous improvements for cell analyzers utilizing the flow cytometric technique. However, inasmuch as a sorting apparatus such as described herein is significantly beneficial when cell analysis and sorting are combined, the preferred embodiment of the present invention will be described in conjunction with cell or particle analysis.

FIG. 1 represents a schematic flow path for moving particles in one analyzer that falls within the purview of the present invention. It is appreciated that the schematic illustration of FIG. 1 represents merely one approach for analyzing and sorting cells using the flow cytometric technique, and that many variations of the embodiment of FIG. 1 may be utilized in conjunction with the present invention. The full details of the analyzer schematically represented in FIG. 1 have been described in a commonly assigned patent application, Ser. No. 276,738, filed on June 24, 1981.

Turning now to the details of FIG. 1 herein, sorting apparatus 10 includes a flow manifold assembly 15 which is designed to provide a stream of flowing liquid containing the particles or cells to be analyzed and sorted. Flow manifold assembly 15 is preferably fabricated in two parts, an upper portion 16 and a lower portion 18. These portions are preferably separable so that a liquid chamber 20 may be inserted and removed, for interchangeability, within the flow paths inside the flow manifold assembly. A sample injection manifold 21 in the embodiment being described depends downwardly so that a container 22 carrying the particles to be analyzed may be inserted thereon. An O-ring 24 is included on the sample injection manifold 21 to assure a liquid-tight fit between the injection manifold and the container.

A main flow cavity 26 is included in the flow manifold assembly and is normally substantially larger in diameter than flow chamber 20. To facilitate smooth, laminar flow the main flow cavity includes a tapered segment 28 converging toward flow chamber 20. Depending into main flow cavity 26 is a sample tube 29 with a lumen 30 extending therethrough. Tube 29 also includes a tapered segment 31 which tapers toward flow chamber 20. In order to provide proper flow and avoid mixing of the sampling liquid and sheath liquid, tapered segment 31 is positioned inside the main flow cavity to leave a short space between its end and flow chamber 20. The opposite end 32 of the sample tube extends beyond injection manifold 21 so that it will be submerged inside sampling liquid 34 within container 22. The sampling liquid includes particles or cells 33 dispersed throughout which are to be analyzed and sorted.

A channel 35 communicates with main flow cavity 26. Liquid is delivered to the main flow cavity through channel 35 to serve as an outer sheath for particles flowing in the liquid stream. Sheath liquid 36 is generally pressurized as it flows through channel 35. Further, sheath liquid 36 should be substantially particle free so that it does not interfere with the analysis of the particles and should be capable of carrying an electrical current so that a potential can be applied across the orifice of the flow chamber for particle analysis purposes. A saline solution is desirably utilized as the sheath liquid.

On the side of flow chamber 20 opposite from main flow cavity 26, another channel 38 is provided in the flow manifold assembly. Channel 38 is in fluid communication with the outlet end of flow chamber 20. A secondary sheath liquid flows through channel 38 normally at a slightly lower pressure than the flow of sheath liquid 36 in channel 35. Once again, a saline solution is desirably employed as secondary sheath liquid 39. A pair of hollow concentrically arranged tubes 40 and 41 are positioned inside the flow manifold assembly so that they are in fluid communication with channel 39, and so that their interior ends are in close juxtaposition with the outlet end of flow chamber 20. Tubes 40 and 41 are designed to facilitate the sorting of the particles after analysis, and will be described in greater detail hereinafter.

A drain channel 42 communicates with main flow cavity 26 and includes a valve 44 which is normally closed during the main flow of liquid through the manifold assembly. Drain channel 42 is provided to drain liquid from the manifold assembly after the flow operations have been completed, and also allows a reverse flow of liquid through flow chamber 20 and main cavity 26 in order to dislodge any particles or other impediments which may be causing a blockage therein.

Another flow channel 45 extends through flow manifold assembly 15 and terminates in an opening 46 in sample injection manifold 21 alongside sample tube 29. When container 22 with particles 33 and sampling liquid 34 therein is connected to the sample injection manifold, pressurized air is delivered through channel 45. Normally, the air is delivered through channel 45 at a slightly higher pressure than that of sheath liquid 36. Under this air pressure, sampling liquid 34 is driven through lumen 30 of the sample tube upwardly (in the embodiment being described as seen in FIG. 1) toward main flow cavity 26. As sampling liquid 34 exits tapered end 31 of the sampling tube, there is a confluence between the sampling liquid and the sheath liquid. A coaxial, bicomponent liquid stream is formed, preferably at velocities in the laminar flow region. It can be seen that the sampling liquid containing the particles to be analyzed forms the inner component of the flowing liquid stream. By the time the stream of liquid enters flow chamber 20, there is substantial equilibration in the velocities of the sheath liquid and the sampling liquid. Moreover, particles 33 in the inner sampling liquid flow in the center of the liquid stream, and are maintained away from the walls of the orifice inside the flow chamber. Electrodes 47 and 48 are positioned in channels 36 and 38, respectively, in order to provide an electrical potential across the orifice of the flow chamber in accordance with the well-known Coulter principle.

Figure 2:
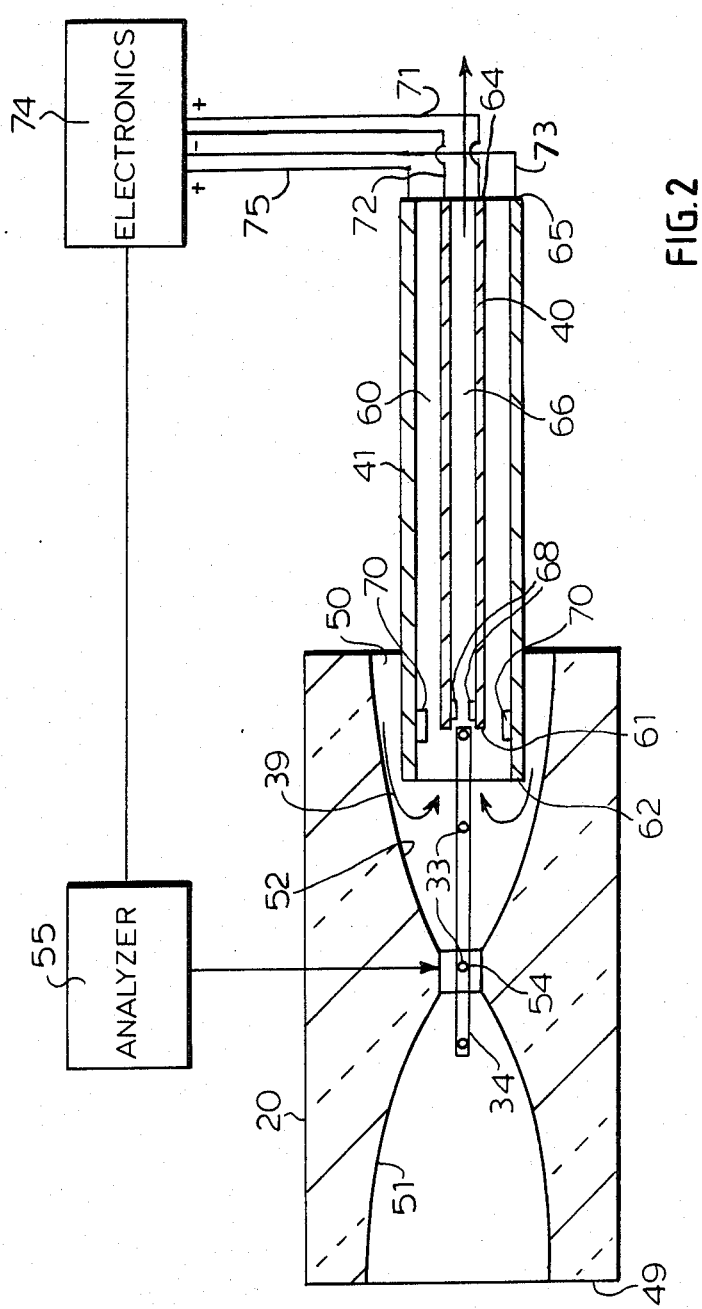
FIG. 2 is an enlarged sectional view of the particle analysis area and the preferred elements for sorting the particles of gas actuation after analysis, illustrating the normal flow of particles therethrough.

Referring now to FIG. 2, taken in conjunction with FIG. 1, the preferred embodiment of flow chamber 20 and the sorting tubes 40 and 41 are schematically illustrated. It can be seen that flow chamber 20 is preferably cylindrically shaped with a passageway extending therethrough. There is an inlet opening 49 and an outlet opening 50 on opposite ends of the flow chamber. A smooth tapering recess 51 communicating with inlet opening 49 extends inwardly inside the flow chamber; on the other side of the flow chamber, a smooth tapering recess 52 communicating with outlet opening 50 extends inwardly inside the flow chamber. Interconnecting recesses 51 and 52 to establish a liquid flow path is a small diameter orifice 54. This orifice is preferably concentrically positioned within the flow chamber so that it lies on the longitudinal axis thereof. The configuration of the flow chamber thus permits the utilization of the well-known Coulter principle, as alluded to above. Both the utilization of the Coulter principle for determining the volume of the particles passing through the orifice and the application of light through the flow chamber for detecting light emitting characteristics of the flowing particles are fully described in the aforementioned commonly assigned pending patent application, Ser. No. 276,738, filed on June 24, 1981. An analyzer 55 has been designated herein as referring to the elements which analyze the particles as they are flowing to detect different parameters thereof.

After particles 33 have been analyzed by flowing through the orifice of flow chamber 20, the particles, within liquid stream 34, flow toward outlet opening 50. In order to sort the particles into different categories as determined by the analyzer, tubes 40 and 41 are provided as generally described above. Specifically, tube 40 is a hollow inner tube and tube 41 is a hollow outer tube concentrically arranged around the inner tube with an annular space 60 therebetween. These tubes are mounted in flow manifold assembly 15 (as schematically illustrated in FIG. 1) so that inner tube 40 has its longitudinal axis aligned substantially with the stream of particles 33, as more clearly seen in FIG. 2. Further, each tube has a particle entrance end 61 and 62, respectively, located just inside outlet opening 50 and as close as possible to orifice 54 (the region wherein the particles are analyzed). Furthermore and preferably speaking, particle entrance end 61 of the inner tube is axially offset or displaced from entrance end 62 of the outer tube. Accordingly, entrance end 62 lies closer to orifice 54. This arrangement of the particle entrance ends facilitates deflection of the particles into annular space 60 between the tubes, as described more completely hereinafter. The trailing ends of the tubes 64 and 65, respectively, are open and lead to individual collection containers (not shown) so that particles may be collected separately into different categories depending upon the flow through the passageway 66 inside the inner tube or through annular space 60 separating the tubes.

A pair of electrodes 68 is positioned on the interior surface of the inner tube just inside the entrance end thereof; electrode pair 70 is positioned on the interior surface of the outer tube just inside its entrance end. Electrode pair 70, however, is not required for operability of the present invention, and is included in the embodiment being described to further develop the scope of the invention. The electrode pairs on the respective tubes generate gas bubbles in the flowing liquid stream as will be described more completely hereinafter. It should be understood that, while a pair of electrodes is preferably utilized on the tubes for gas bubble generation, the invention remains operable by employing only one electrode on the inner tube which generates bubbles to block the entrance to the inner tube. The electrodes are preferably made of platinum for optimal performance to generate gas bubbles in a flowing liquid electrode medium. Electrical lead wires 71 and 72 are connected to electrodes 68 and lead wires 73 and 75 are connected to electrodes 70 in order to establish connections to the requisite positive and negative poles, and are further connected into the electronic circuitry 74 which controls the operation of the respective electrodes during operation of the instant apparatus. The electronics are further connected with analyzer 55 so that the generation of gas bubbles by the electrodes is coordinated with the particle analysis. One approach of handling the electronics of the present invention with the gas generating electrodes, together with analyzer coordination, is described in the aforementioned Zold patent, U.S. Pat. No. 4,175,662.

Normal operation of the instant sorting apparatus is illustrated in FIG. 2. After particles 33 have been analyzed by passing through orifice 54, they normally are directed into passageway 66 of inner tube 40. This is the normal flow path of the particles irrespective of the operation of the analyzer. Secondary sheath liquid 39 is flowing outside of outer tube 41 in a direction opposite the flowing stream of particles. As described above, inasmuch as the pressure of the flowing sheath liquid is slightly lower than the pressure of the particle suspension flowing through the flow chamber, sheath liquid 39 is caused to flow toward entrance ends 61 and 62 of the tubes thereby assisting the flow of particles into the tubes. In normal operation, the flow of particles would be directed into entrance end 61 of the inner tube. Electrical impulses transmitted from the electronics to electrodes 70 activate gas bubbles at the entrance of the annular space between the inner and outer tubes thereby blocking any particles from flowing thereinto; accordingly, particle flow will be directed into passageway 66 of the inner tube. It is understood that operation of gas generating electrodes 70 may not be necessary for particle flow into the inner tube, but may serve as a supplementary mechanism to assure such flow. Particles passing through passageway 66 may be collected in a collection container as representative of particles of a certain category.

Figure 3:
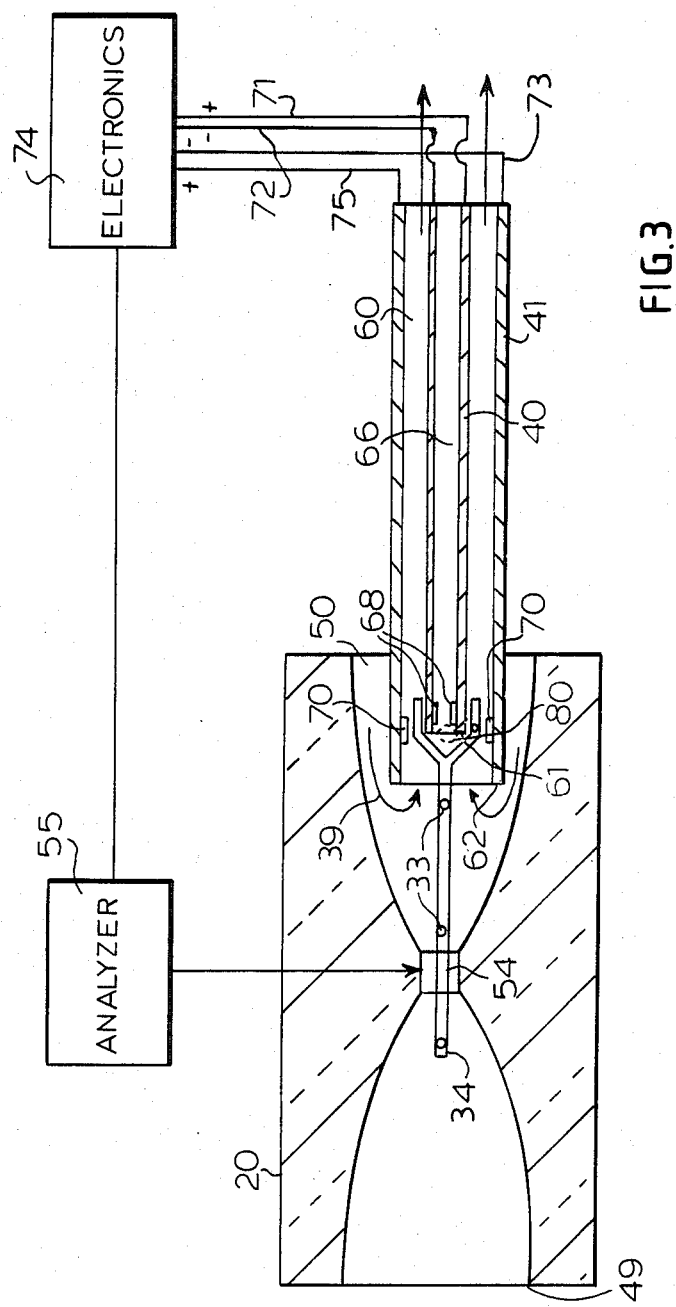
FIG. 3 is an enlarged sectional view similar to the view of FIG. 2 illustating the deflection of particles into a different flow path by gas actuation for sorting purposes.

FIG. 3 illustrates the ability of the present invention to sort particles in the flowing stream. For instance, when particles passing through orifice 54 are determined by analyzer 55 to have certain pre-determined or different parameters, this information is electrically fed into electronics circuitry 74. Electrical impulses are provided to gas generating electrodes 68 which, when activated, cause gas bubbles 80 to occur at the proper time to block entrance end 61 of the inner tube. Accordingly, the gas bubbles prevent certain particles, determined in accordance with the information from the analyzer, from entering the inner tube. Further, the occurrence of gas bubbles deflects the flowing particles into annular space 60 between the inner and outer tubes. It can be seen that the offset nature at the entrance ends of the inner and outer tubes facilitates this deflection of particles into the annular space. Each particle in the annular space then passes out of the tube arrangement and is collected separately from those particles passing through the inner tube. In this fashion, particles having different or pre-determined parameters may be collected into different categories. It is understood that the sorting of the particles is performed rapidly so that there is rapid shifting of particle flow between flow through the inner tube and flow through the annular space between the tubes for different categorizations of particles.

An alternative embodiment of the present invention, particularly in the sorting elements, is illustrated in FIG. 4. The base numerals for the various elements of this embodiment are the same as the previously described embodiment, followed by the suffix "a". In this embodiment, electrode pairs 68a and 70a are positioned inside the inner and outer tubes, respectively, at the tube ends distal from the entrance ends. Thus, electrode pairs 68a and 70a are located at ends 64a and 65a of the respective tubes. Gas bubbles generated by electrodes 68a or 70a serve to obstruct fluid flow diverting particle flow from inner tube space 66a to annular space 60a or the reverse. This remote location of the electrodes simplifies construction of the tubes because the electrodes are located in an area of the device where size of the components might be much less critical. The arrangement of electrodes at the remote ends of the tubes is advantageous in a Coulter-type volume sensing analyzer since electrical isolation of the bubble generating electrical pulses may be improved. Such improvement is related to the greater distance between gas generating electrodes and the Coulter orifice.

Further, although the preferred embodiment of the present invention, as described above, utilizes electrodes as the gas bubble generating source, other techniques for gas generation fall within the purview of the present invention. For instance, and in addition to electrolysis, gas bubbles may be generated by thermal means, such as resistance heating, absorption of light, microwave or RF heating, chemical reactions and decompositions, or even direct gas injection into the respective tubes.

Thus, the present invention provides a sorting apparatus which utilizes a gas generation technique to deflect the flow path of flowing particles so that particles having different parameters may be sorted and subsequently collected according to their different categorizations.

What is claimed is:

1. An apparatus for sorting particles moving in a liquid stream according to differences in particle parameters comprising:
   means for providing a stream of particles in a liquid flow;
   means for analyzing said particles as they are flowing to detect particles having different parameters;
   a hollow inner tube and a concentrically arranged hollow outer tube located downstream of said analyzing means, said inner and said outer tubes having substantially concentric particle exit ends separated by an annular space, said inner tube having its longitudinal axis aligned substantially with said stream of particles;
   means for generating gas bubbles in said inner tube to prevent particles from flowing therein and to deflect flowing particles into the annular space between said inner and outer tubes; and
   means for coordinating the generation of gas bubbles with said particle analysis to selectively deflect particles having said different parameters into said annular space whereby the particles are sorted for collection from the exit ends of said tubes.

2. The apparatus of claim 1 wherein said particles are analyzed in a sensing region as they pass therethrough, said tubes being located downstream of said sensing region so that undeflected particles are adapted to flow through said inner tube for collection thereof.

3. The apparatus of claim 2 wherein the particle entrance ends of said tubes are offset from each other, the entrance end of said outer tube being closer to said sensing region to facilitate deflection of particles into the annular space between said tubes.

4. The apparatus of claim 1 wherein said means for generating gas bubbles is at least one electrode located in the inner tube, said electrode being activatable by said coordinating means to produce gas bubbles corresponding to the deflection of particles into said annular space.

5. The apparatus of claim 4 wherein said electrode is located in said inner tube remotely from the entrance end into which particles flow.

6. The apparatus of claim 4 in which a pair of electrodes is located in the inner tube.

7. The apparatus of claim 1 which further includes means for generating gas bubbles in the annular space between the inner and outer tubes to confine the stream of particles to flow into the inner tube.

8. An apparatus for sorting particles comprising:
   means for transporting particles in a stream;
   first particle conduit means into which said stream is normally directed; and
   actuatable means for preventing particles from passing into said first particle conduit means and for directing said prevented particles into second particle conduit means surrounding said first particle conduit means, said first and said second conduit means having substantially concentric particle exit ends separated by an annular space for the passage of said prevented particles for sorting purposes.

9. An apparatus for sorting particles comprising:
   means for transporting particles in a stream;
   first particle conduit means into which said stream is normally directed; and
   actuatable means located remotely from an end of said conduit means into which said stream flows for preventing particles from passing into said first particle conduit means and for directing said prevented particles into second particle conduit means surrounding said first particle conduit means.

10. A method of sorting particles moving in a liquid stream according to differences in particle parameters comprising:
   flowing particles in a liquid stream;
   analyzing said particles as they are flowing to detect particles having different parameters;
   directing said particles into a hollow inner tube located downstream of the area where the particles are analyzed;
   generating gas bubbles in said inner tube to prevent particles from flowing therein and to deflect flowing particles into an annular space between said inner tube and a concentrically arranged outer tube;
   coordinating the generation of gas bubbles with said particle analysis to selectively deflect particles having said different parameters into said annular space; and collecting particles from an exit end of said inner tube and particles having different parameters from the annular space at the exit end of said outer tube whereby the particles are sorted.

11. The method of claim 10 wherein said generating step includes producing gas bubbles by at least one electrode located in the inner tube.

12. The method of claim 11 wherein gas bubbles are produced by a pair of electrodes located in the inner tube.

13. The method of claim 10 wherein said bubbles are produced by at least one electrode located in said inner tube remotely from the particle entrance end into which particles flow.

14. The method of claim 10 which further includes generating gas bubbles in the annular space between the inner and outer tubes to confine the stream of particles to flow into the inner tube.

15. The method of claim 10 which further includes moving sheath liquid outside of said outer tube in a direction opposite the flowing stream of particles and causing said sheath liquid to flow toward the entrance ends of said tubes to assist the flow of particles into said tubes.

16. The method of claim 10 which further includes collecting the particles sorted respectively into said inner tube and said annular space in separate containers.

17. A method of sorting particles comprising:
moving particles in a stream;
normally directing said stream into first particle conduit means;
preventing selected particles from passing into said first particle conduit means;
directing said prevented particles into second particle conduit means defined by an annular space surrounding said first particle conduit means; and
collecting particles from an exit end of said first particle conduit means and selected particles from an annular space at the exit end of said second particle conduit means whereby the particles are sorted.

* * * * *